United States Patent [19]

Sakamoto

[11] Patent Number: 6,063,058
[45] Date of Patent: May 16, 2000

[54] LIQUID MEDICINE CONTINOUS INFUSER

[75] Inventor: Katsumi Sakamoto, Yokohama, Japan

[73] Assignee: Piolax, Inc., Kanagawa-ken, Japan

[21] Appl. No.: 09/203,936

[22] Filed: Dec. 2, 1998

[30] Foreign Application Priority Data

Mar. 12, 1997 [JP] Japan .................................. 9-348466

[51] Int. Cl.$^7$ ................................................ A61M 37/00
[52] U.S. Cl. .................................. 604/132; 128/DIG. 12
[58] Field of Search .................................. 604/131, 132, 604/133, 151, 153; 128/DIG. 12

[56] References Cited

U.S. PATENT DOCUMENTS

| | | |
|---|---|---|
| 3,506,005 | 4/1970 | Gilio et al. . |
| 4,909,790 | 3/1990 | Tsujikawa et al. . |
| 5,649,910 | 7/1997 | Kriesel et al. . |
| 5,807,335 | 9/1998 | Kriesel et al. ............................ 604/131 |
| 5,897,530 | 4/1999 | Jackson .................................. 604/132 |
| 5,921,962 | 7/1999 | Kriesel et al. ............................ 604/132 |
| 5,961,492 | 10/1999 | Kriesel et al. ............................ 604/132 |

FOREIGN PATENT DOCUMENTS

| | | |
|---|---|---|
| 0380862A2 | 6/1989 | European Pat. Off. . |
| 6470069 | 3/1989 | Japan . |

OTHER PUBLICATIONS

European Search Report dated Jun. 23, 1999.
PCT Application dated Oct. 1, 1992.
PCT Application dated Jul 3, 1997.

*Primary Examiner*—John D. Yasko
*Attorney, Agent, or Firm*—Howard & Howard

[57] ABSTRACT

There is disclosed a liquid medicine continuous infuser having a basic structure comprising a bag-shaped member that can apply a pressure to a liquid medicine accommodated inside the infuser, an inflow/outflow section for flowing in and flowing out the liquid medicine, and an area positioned inside the bag-shaped member and having a predetermined volume. The above pressure provides a predetermined characteristic curve in relation to the capacity of the bag-shaped member, and the area having the predetermined volume is for increasing the capacity of the bag-shaped member when the liquid medicine is accommodated inside the bag-shaped member. Further, the bag-shaped member is for applying a pressure to a liquid medicine accommodated inside the bag-shaped member along with the predetermined characteristic curve, with a pressure corresponding to the capacity increased by the area having the predetermined volume, when the liquid medicine is accommodated inside the bag-shaped member used, as an initial value.

9 Claims, 5 Drawing Sheets

LIQUID MEDICINE CONTINOUS INFUSER

BACKGROUND OF THE INVENTION

1. Field of the Invention

The present invention relates to a liquid medicine continuous infuser for giving a liquid medicine to a patient over a long time. More particularly, it relates to a liquid medicine continuous infuser for flowing out a liquid medicine by utilizing a pressing pressure of an elastic bag (balloon).

2. Description of the Related Art

For giving liquid medicine to a patient such as an adult whose physical strength is exhausted, liquid medication systems take many hours to match the physical strength condition of the patient in treating the disease. Such liquid medicine may include, for example, an anticancer drug, an anodyne, a local anesthetic, a blood sugar level adjuster, etc. Each of these liquid medicines is delivered to a patient through a vein, an artery, a subcutaneous tissue, or by use of an epidural injection.

As one of such liquid medication systems, there has been disclosed a liquid medicine continuous infuser or a fountain syringe for continuously flowing out a liquid medicine by utilizing the pressing pressure of a balloon, as disclosed in Japanese Patent Application Laid-Open No. 64-70069. This liquid medicine continuous infuser comprises a cylindrical external axis, an internal axis slidably accommodated within this external axis and a cylindrical balloon with its both ends fixed air-tight at an outer periphery of these axes. A flow rate controller, a tube, a liquid medicine injecting needle, etc. are connected sequentially to an opening of the external axis through a three-directional stop cock.

A liquid medicine to be given to a patient is filled into the balloon through the three-directional stop cock, the external axis and a gap between the external axis and the internal axis. The liquid medicine is then passed through the flow rate controller, the tube, the adapter, etc. after having been switched over by the three-directional stop cock. Finally the liquid medicine is delivered to the patient through a vein or other route by a liquid medicine injecting needle. At the time of charging the liquid medicine into the balloon, the internal axis is projected from the external axis along with the charging of the liquid medicine. Thus, the capacity of the balloon can be made larger by inflating the balloon not only in a radial direction but also in an axial direction. Also, at the time of finishing the medication of the liquid medicine, the internal axis is accommodated within the external axis and the balloon is contracted into an axial direction, so that a remaining volume of the liquid medicine can be made smaller.

It is desirable that the volume of the liquid medicine remaining in the liquid medicine continuous infuser after finishing the medication is as small as possible to ensure a secure medication and avoiding an occurrence of unused liquid medicine. However, the liquid medicine continuous infuser having the above-described structure cannot meet the above requirement satisfactorily. Thus it is desired to provide a novel liquid medicine continuous infuser that can effectively reduce the volume of the liquid medicine remaining in the infuser after finishing a medication.

Further, from the viewpoint of achieving proper medication, it has also been desired to provide a liquid medicine continuous infuser that can maintain a substantially constant level of a liquid medicine given to a patient without a sudden variation in the volume of the liquid medicine during medication.

SUMMARY OF THE INVENTION

It is an object of the present invention to provide a liquid medicine continuous infuser that can effectively flow out a liquid medicine by keeping a stable outflow level to the last moment and that can reduce the volume of the liquid medicine remaining in the infuser to an extremely low level at the time of finishing the medication.

In an attempt to achieve the above object, the inventor of the present invention has carried out various investigations by using the liquid medicine continuous infuser as disclosed in Japanese Patent Application Laid-Open No. 64-70069 and has found that this infuser has the following characteristics.

FIG. 1 is a characteristic diagram for showing a relationship between a capacity C of the balloon of the liquid medicine continuous infuser and a contraction pressure P of the balloon, where the horizontal axis shows a capacity level of the balloon and the vertical axis shows a contraction pressure. In this diagram, when the capacity of the balloon increases, the contraction pressure increases suddenly from a free state (r0) where the contraction pressure is zero (0), then the contraction pressure reaches a peak of a maximum value (r4) and decreases once thereafter to take a minimum value (r2) as shown in a range T2.

Then, when the balloon capacity increases further, the contraction pressure increases gradually as shown in a range T1.

This fact corresponds to a fact that every one can experience at the time of inflating a rubber balloon. It initially requires relatively large power to expand the film of the balloon, since near to its relaxed state the balloon maintains almost an intrinsic film thickness of the balloon. Then, after this state, it does not require so much large power to further expand the film of the balloon as the film thickness is small once the balloon has been inflated to a certain level.

According to a further investigation by the inventor, it has been made clear that in the liquid medicine continuous infuser having the above-described characteristics, a liquid medicine is charged into the balloon to inflate the balloon so as to reach a predetermined balloon capacity (r1) larger than the capacity of the balloon corresponding to the peak (r4) of the contraction pressure as shown in a range T3, and thereafter, the balloon is made to shrivel to a relaxed state where the contraction pressure is zero (r0), during period which the liquid medicine is flowed out.

Accordingly, it can be concluded that, according to the conventional liquid medicine continuous infuser that is used in the above-described manner, a liquid medicine of the volume corresponding to the balloon capacity shown in a range T5 is left in the balloon so that the whole volume of the liquid medicine cannot be flowed out. This is true since the internal space of the balloon does not disappear completely even if the balloon has shriveled to its relaxed state (r0).

Further, in the above using state, the liquid medicine outflow has to pass through an area of the range T2 where the contraction pressure changes suddenly, so that the flow rate of the outflowing liquid medicine is lowered suddenly when approaching the free state (r0). This makes it difficult to maintain an essentially constant outflow level of the liquid medicine and becomes an obstacle to elimination of the remaining liquid medicine as well.

A liquid medicine continuous infuser according to the present invention has been made based on the above-described results of the investigations. The infuser has a basic structure comprising a bag-shaped member that can apply a pressure to a liquid medicine accommodated inside the infuser, an inflow/outflow section for flowing in and flowing out the liquid medicine, and an area positioned inside the bag-shaped member and having a predetermined volume.

The above pressure provides a predetermined characteristic curve in relation to the capacity of the bag-shaped member, and the area having the predetermined volume is for increasing the capacity of the bag-shaped member when the liquid medicine is accommodated inside the bag-shaped member.

Further, the bag-shaped member is for applying a pressure to a liquid medicine accommodated inside the bag-shaped member along with a predetermined characteristic curve, with a pressure, corresponding to the capacity increased by the area having the predetermined volume when the liquid medicine has been accommodated inside the bag-shaped member used, as an initial value.

With the above-described structure, it is possible to provide a liquid medicine continuous infuser that can effectively flow out a liquid medicine at a stable outflow rate to the last moment and that can reduce the remaining volume of the liquid medicine to an extremely low level at the time of finishing its medication.

More specifically, the liquid medicine continuous infuser according to the present invention has an inner bag into which a liquid medicine is to be charged, and the inner bag can be disposed inside the bag-shaped member. In this case, it is preferable that the bag-shaped member is an elastic bag and that the area positioned inside the bag-shaped member, and having a predetermined volume, is formed by a fluid disposed between the elastic bag and the inner bag.

Based on the above structure, it becomes possible to effectively reduce the remaining volume of the liquid medicine, as the inner bag is pressed to be shriveled by a volume corresponding to the volume of the fluid even if the elastic bag moves to its relaxed free state. Further, based on the existence of the fluid, the section of T1 in FIG. 1 can be set longer and the flow rate of the outflowing liquid medicine can be made constant.

In this case, it is more preferable that the sum of the volume of the fluid and the volume of the inner bag when the inner bag is shriveled completely is larger than the capacity of the elastic bag in its free state, in order to reduce the remaining volume of the liquid medicine more securely and to further stabilize the flow rate of the outflowing liquid medicine.

On the other hand, more specifically, it is also possible to have such a structure that the bag-shaped member is an elastic bag and that the area positioned inside the bag-shaped member and having a predetermined volume is formed by a core disposed inside the elastic bag.

Based on the above structure, the pressing pressure of the elastic bag will not decrease suddenly, as the elastic bag is in a state inflated by the core even if the elastic bag approaches its relaxed state and there remains almost no volume of the liquid medicine. In other words, it is possible to apply a practically constant pressing pressure to a liquid medicine during a period from the start to the finish of the medication, so that the flow rate of the outflowing liquid medicine can be made practically constant and almost all the volume of the liquid medicine within the elastic bag can be flowed out, thereby effectively preventing of liquid medicine remaining.

In this case, it is more preferable that the volume of the core is larger than the capacity of the elastic bag in its relaxed state, for the purpose of reducing the remaining volume of the liquid medicine more securely and for more stabilizing the flow rate of the outflowing liquid medicine.

Further, the liquid medicine continuous infuser according to the present invention can also take such a structure that the bag-shaped member is an elastic bag having a pair of mutually opposite flat surfaces and a peripheral wall for connecting the pair of flat surfaces, thus forming a flat bag shape as a whole. The thickness of each of the pair of flat surfaces is larger than the thickness of the peripheral wall at least at a center portion of each of the pair of flat surfaces.

Based on the above structure, it is possible to provide a liquid medicine continuous infuser having a flat shape as a whole when a liquid medicine is filled into the infuser as mainly the peripheral wall is deformed, so that a user can carry the infuser in his or her pocket or an accessory case.

In this case, it is preferable that the thickness of each of the pair of flat surfaces gradually decreases in the vicinity of a portion where the flat surfaces are connected to the peripheral wall from the viewpoint of achieving a more flat shape as a whole.

Further, the liquid medicine continuous infuser according to the present invention can also take such a structure that the bag-shaped member is an elastic bag and this elastic bag has a pair of mutually opposite flat surfaces and a peripheral wall for connecting the pair of flat surfaces, thus forming a flat bag shape as a whole. There may also be provided a panel member having a higher stiffness than that of the elastic bag on the pair of flat surfaces.

Based on the above structure, it is possible to provide an easily portable liquid medicine continuous infuser having a flat shape as a whole when a liquid medicine is filled into the infuser, as the panel member restricts inflating of the flat surfaces.

In the liquid medicine continuous infuser of the present invention, it is preferable that the inflow/outflow section is an inflow/outflow opening provided corresponding to the peripheral wall of the elastic bag, for achieving a flat shape as a whole and for facilitating a user to carry the infuser, when it is placed in a pocket or an accessory case, by facing the outflow opening to an opening of the pocket. This also achieves a secure inflow/outflow of the liquid medicine.

DETAILED DESCRIPTION OF THE PREFERRED EMBODIMENTS

Each of embodiments of the present invention will be explained in detail below with reference to the drawings.

At first, a first embodiment of a liquid medicine continuous infuser of the present invention will be explained mainly with reference to FIGS. 2A to 4.

Figure 2A:
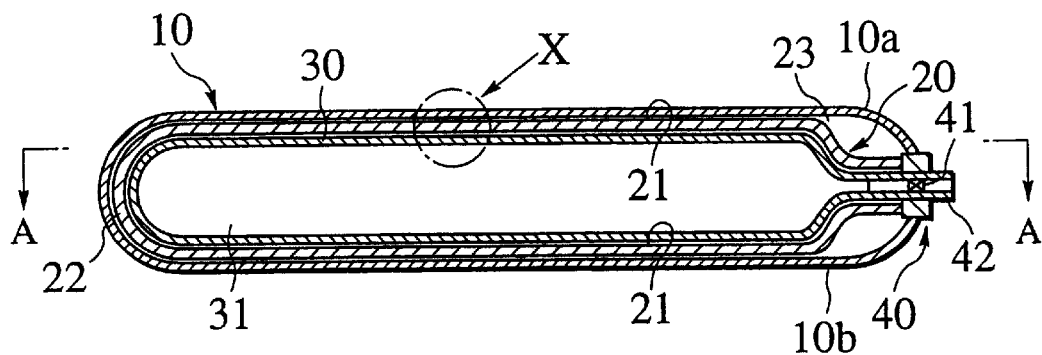
FIG. 2A is a side cross-sectional view for showing a state of a liquid medicine continuous infuser charged with a liquid medicine according to a first embodiment of the present invention.
Figure 2B:
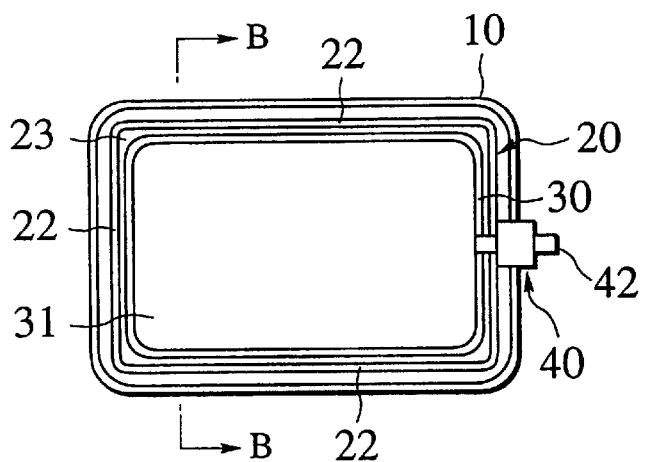
FIG. 2B is a cross-sectional view cut along an A—A line of FIG. 2A.
Figure 2C:
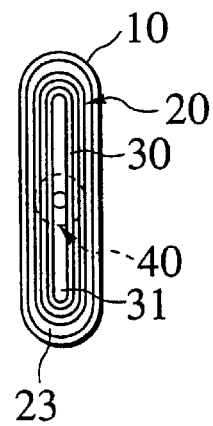
FIG. 2C is a cross-sectional view cut along a B—B line of FIG. 2B.
Figure 2D:
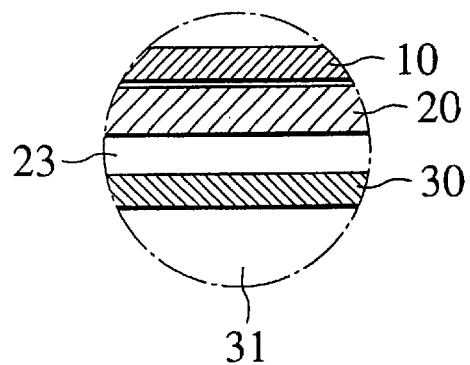
FIG. 2D is an enlarged cross-sectional view of an X portion of FIG. 2A.
Figure 3:
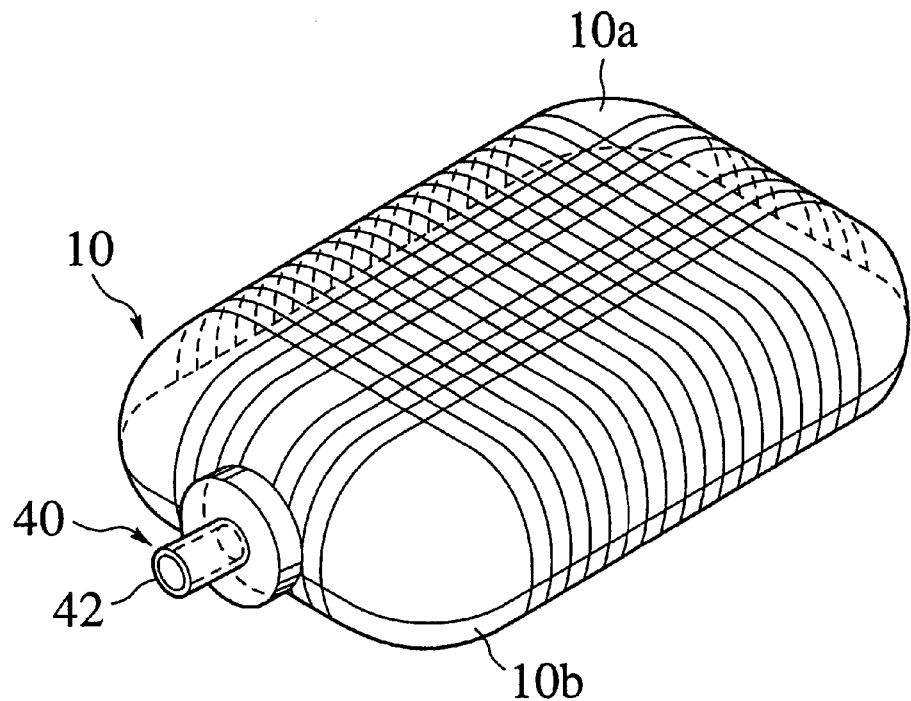
FIG. 3 is a perspective view for showing an appearance of the liquid medicine continuous infuser of the same embodiment.
Figure 4:
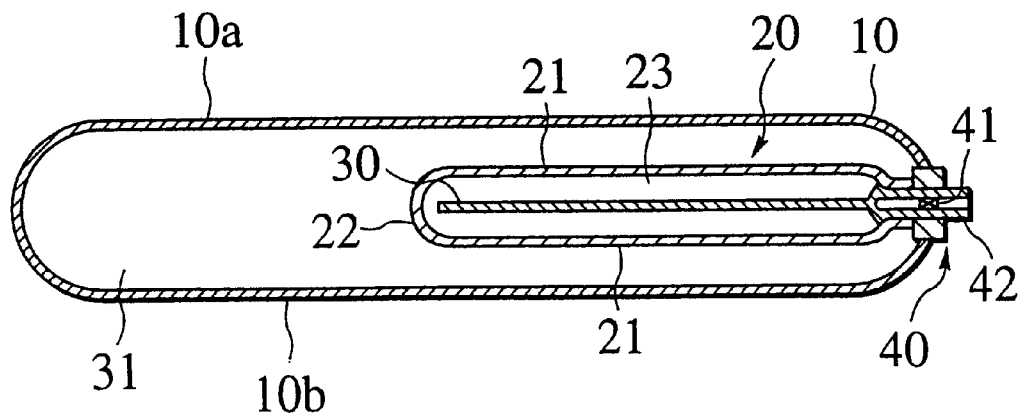
FIG. 4 is a side cross-sectional view for showing a state of the liquid medicine continuous infuser with the liquid medicine flowed out completely in the same embodiment.

FIGS. 2A to 2D show states of a liquid medicine continuous infuser charged with a liquid medicine; FIG. 2A is a side cross-sectional view, FIG. 2B is a cross-sectional view cut along an A—A line of FIG. 2A, FIG. 2C is a cross-sectional view cut along a B—B line of FIG. 2B, FIG. 2D is a partially enlarged cross-sectional view of FIG. 2A, FIG. 3 is a perspective view for showing an appearance of the liquid medicine continuous infuser, and FIG. 4 is a side cross-sectional view for showing a state of the liquid medicine continuous infuser with the liquid medicine flowed out completely.

The liquid medicine continuous infuser of the present embodiment has a protection case 10 made of a synthetic resin, a metal and the like to form a flat pillow shape as a whole. At an end, in a longitudinal direction, of the protection case 10, there is provided a liquid inflow/outflow opening 40 having its opening 42 stretched to the outside. The protection case 10 is structured by two members of an upper member 10a and a lower member 10b which can be opened or closed by hinges not shown and can be fixed in a closed state by a stopper not shown.

Within the protection case 10, there is disposed an elastic bag 20 made of an elastic material such as a natural rubber or a synthetic rubber to form a flat bag shape as a whole. In the drawings, 21 denotes a pair of flat surfaces of the elastic bag 20, and 22 denotes a peripheral wall for connecting the pair of flat surfaces 21. Further, inside the elastic bag 20, there is disposed an inner bag 30 to be filled with a liquid medicine 31. A bag of an elastic material similar to that of the elastic bag 20 is preferably employed for the inner bag 30. This bag may also be the one formed by a synthetic resin film or a synthetic resin film laminated by a metal foil or the like. However, when a synthetic resin film having no elasticity is used, the inner bag 30 is formed to have the content capacity of the state that the liquid medicine 31 is filled to the full. When a natural rubber or a synthetic rubber is used for the inner bag 30, it is desirable to have a chemical resistant film such as a silicon rubber or the like formed on the inner surface of the inner bag so as to prevent an additive or the like in the rubber from being solved into the liquid medicine 31.

The liquid medicine inflow/outflow opening 40 projecting from the end of the protection case 10 is formed by a tubular member in the present embodiment, and this tubular member pierces through an end part formed on the peripheral wall 22 of the elastic bag 20, is connected to an end of the inner bag 30 and is introduced into the inner bag 30. The elastic bag 20 is connected air-tight to an outer periphery of the liquid medicine inflow/outflow opening 40. A check valve 41 is disposed within the liquid medicine inflow/outflow opening 40. The check valve 41 has a structure like an air injection opening of a tire of an automobile, for example, and a valve of the check valve 41 opens at the time of injecting the liquid medicine into the inside from the outside and closes when the liquid medicine tries to outflow from the inside. At the time of medicating the liquid medicine 31 to a patient, a pipe-shaped injection port connected to a medication tube or the like is inserted into the check valve from the outside to cancel the check, so that the valve is opened compulsively to flow out the liquid medicine 31.

Further, in the present embodiment, there is sealed a fluid 23 selected from a liquid such as water and a gas such as air into a gap between the elastic bag 20 and the inner bag 30. The sum of the volume of the fluid 23 and the volume of the inner bag 30 when it is shriveled completely is made larger than the content capacity of the elastic bag 20 in its relaxed state. As a result, the elastic bag 20 is structured to give a pressing pressure to the outer periphery of the inner bag 30 even in the state that the inner bag 30 is not filled with the liquid medicine 31. In the case of the present embodiment, the content capacity of the elastic bag 20 is set to the state of r2 in FIG. 1 by the volume of the inner bag 30 and the fluid 23 even in the state that the liquid medicine 31 is not filled in the inner bag 30.

In the liquid medicine inflow/outflow opening 40, there may be provided a three-directional stop cock capable of switching the passage of the liquid medicine 31, instead of the check valve 41. In other words, it is possible to arrange such that a syringe for injecting a liquid medicine and a medication tube are connected to the three-directional stop cock, then the liquid medicine is filled into the inner bag 30 from the syringe through the three-directional stop cock, a passage of the three-directional stop cock is opened at the medication tube side, and the liquid medicine inside the inner bag 30 is sent to the medication tube for achieving the medication.

As the liquid medicine inflow/outflow opening 40, this may also be the one separately provided with a liquid medicine inflow opening and a liquid medicine outflow opening. In this case, the liquid medicine inflow opening may be provided with a check valve to enable a liquid medicine to be filled into the inner bag 30 by use of the syringe or the like and the liquid medicine outflow opening may be provided with a normal valve unit to open the valve unit at the time of medication.

Further, the liquid medicine inflow/outflow opening 40 is connected with a medication needle through a flow rate control valve, a filter, a medication tube, etc., but not shown. The medication needle is inserted into a vein or other part of a patient to start a medication of the liquid medicine. The above-described structures are known from the disclosure in Japanese Patent Application Laid-Open No. 64-7006 or others, and their explanation will be omitted here.

There will be explained below the operation of the liquid medicine continuous infuser according to the present embodiment at the time of medicating a liquid medicine after the medicine has been filled in the infuser.

In preparation, a syringe such as a hypodermic syringe or the like, not shown, is connected to the opening 42 of the liquid medicine inflow/outflow opening 40 by inserting the syringe into this opening, and the liquid medicine 31 to be given to a patient is injected into the liquid medicine inflow/outflow opening 40 by the syringe or the like. Then, the check valve 41 inside the liquid medicine inflow/outflow opening 40 is opened and the liquid medicine 31 is filled into the inner bag 30. When the liquid medicine 31 has been filled into the inner bag 30 to the full, the elastic bag 20 is inflated to the full inside the protection case 10. Therefore, the elastic bag 20 is inflated along the inner peripheral shape of the protection case 10. Since the protection case 10 has a flat shape, this is easily portable in the pocket or others.

In this state, a pipe-shaped injection opening provided at an end of a medication tube not shown is inserted into the liquid medicine inflow/outflow opening 40, and the medication tube is connected to the liquid medicine inflow/outflow opening 40. Then, the check valve 41 is opened compulsively by the pipe-shaped injection opening. As a result, the liquid medicine 31 inside the inner bag 30 flows out to the medication tube through the liquid medicine inflow/outflow opening 40, and the liquid medicine 31 is given to the patient through his or her vein or other part from the medication needle not shown connected to a front end of the medication tube.

Figure 1:
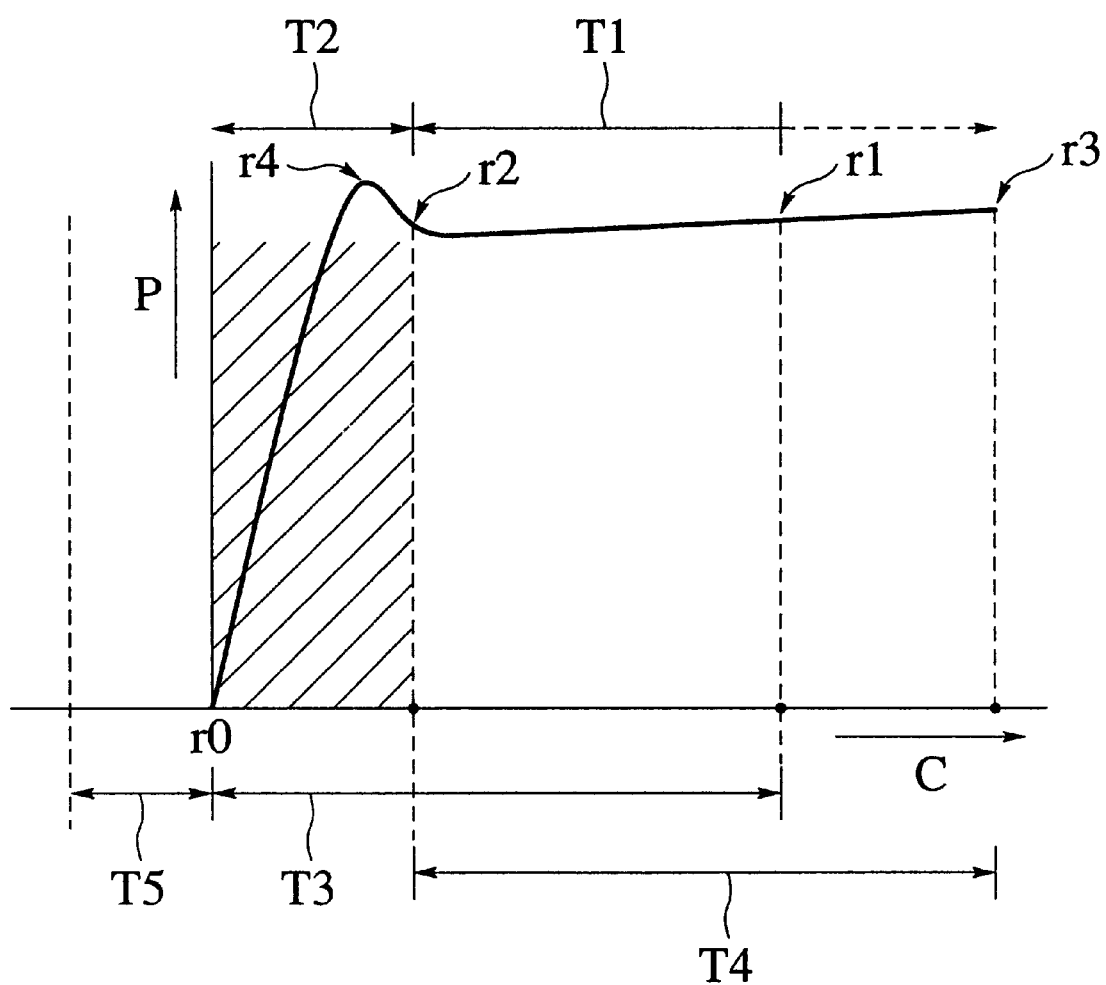
FIG. 1 is a characteristic diagram for showing a relationship between a capacity C and a contraction pressure P of a liquid medicine continuous infuser.

In this case, the content capacity of the elastic bag 20 is set to the state of r2 in FIG. 1 by the volume of the inner bag 30 and the fluid 23 even in the state that the liquid medicine 31 is not filled in the inner bag 30. When the liquid medicine 31 is filled into the inner bag 30, the content capacity of the elastic bag 20 becomes the state of r3 in FIG. 1. Once the medication of the liquid medicine 31 is started, the content volume of the elastic bag 20 changes from the state of r3 to r2 as shown in the section of T4 in FIG. 1 along with the outflow of the liquid medicine 31.

As there is almost no change in the contraction pressure of the elastic bag 20 during the section shown by T4, it is possible to apply almost a constant pressing pressure to the inner bag 30 from the beginning to the end of the medication. As a result, it is possible to make the liquid medicine 31 outflow at almost a constant flow rate from the beginning to the end of the medication. Even if there is left almost no liquid medicine 31 within the inner bag 30, the remaining liquid medicine 31 can be made to outflow to the last dip with almost no volume left in the inner bag 30, as the pressing pressure is kept being applied to the inner bag 30.

Figure 5A:
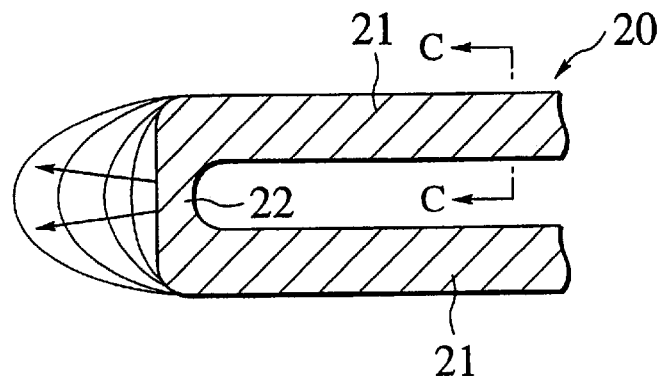
FIG. 5A is a partial lateral cross-sectional view for showing one example of an elastic bag of the liquid medicine continuous infuser of the same embodiment.
Figure 5B:
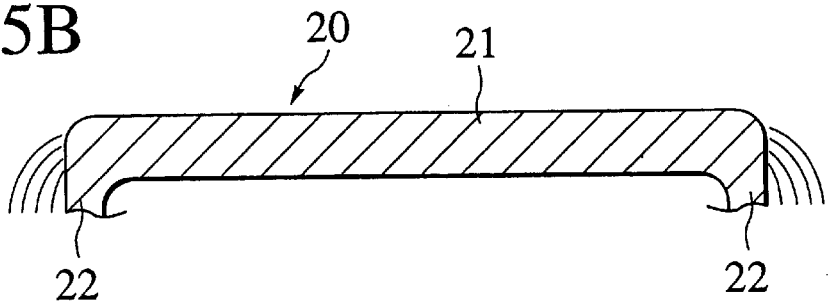
FIG. 5B is a cross-sectional view cut along a C—C line of FIG. 5A.

FIGS. 5A and 5B show one example of a shape of the elastic bag 20 that can be suitably applied to the liquid medicine continuous infuser of the present embodiment. FIG. 5A is a partial lateral cross-sectional view of the elastic bag 20 and FIG. 5B is a cross-sectional view cut along a C—C line of FIG. 5A.

This elastic bag 20 has a flat bag shape as a whole, with the thickness of each of the mutually opposite flat surfaces 21 larger than the thickness of the peripheral wall 22. Accordingly, when a liquid medicine is filled into the inner bag 30, the elastic bag 20 is inflated with the peripheral wall 22 expanded greatly as shown by arrows in the drawing, so that the elastic bag 20 is easily expandable by keeping a flat shape as a whole. As a result, it is possible to inflate the elastic bag 20 in a shape to match more suitably with the inner peripheral shape of the protection case 10.

Figure 6A:
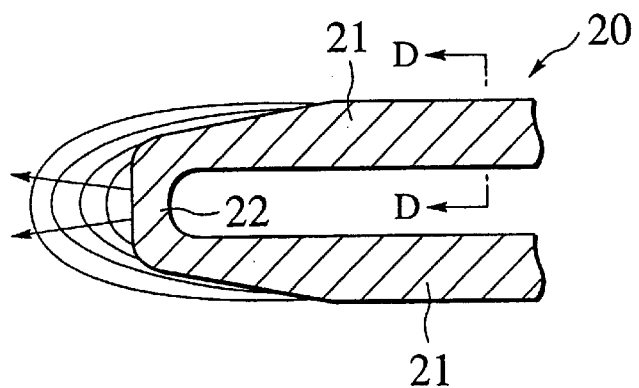
FIG. 6A is a partial lateral cross-sectional view for showing another example of an elastic bag of the liquid medicine continuous infuser of the same embodiment.
Figure 6B:
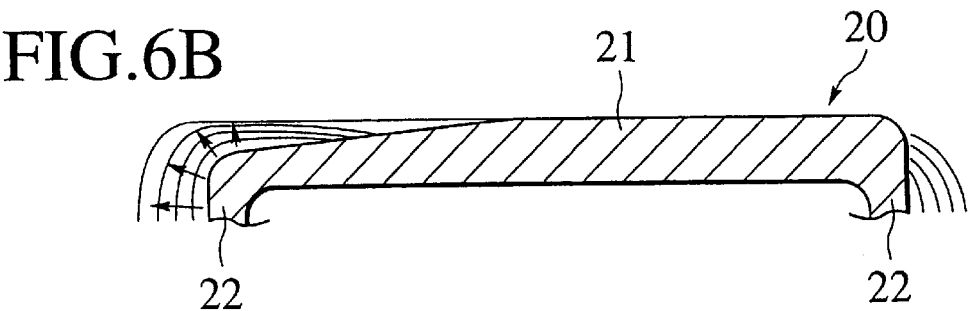
FIG. 6B is a cross-sectional view cut along a D—D line of FIG. 6A.

FIGS. 6A and 6B show another example of a shape of the elastic bag 20 that can be suitably applied to the liquid medicine continuous infuser of the present embodiment. FIG. 6A is a partial lateral cross-sectional view of the elastic bag 20 and FIG. 6B is a cross-sectional view cut along a D—D line of FIG. 6A.

This elastic bag 20 has a flat bag shape as a whole, with the thickness of each of the mutually opposite flat surfaces 21 set gradually smaller at a peripheral edge portion and with the thickness of the peripheral wall 22 also set small. Accordingly, when a liquid medicine is filled into the inner bag 30, the elastic bag 20 is inflated with the peripheral wall 22 expanded greatly as shown by arrows in the drawings, so that the elastic bag 20 is easily expandable by keeping a flat shape as a whole. As a result, it is possible to inflate the elastic bag 20 in a shape to match more suitably with the inner peripheral shape of the protection case 10.

It is also possible to add a panel of a large stiffness such as a synthetic resin panel or a metal panel to at least one of the opposing flat surfaces 21 by adhesion or welding. By this arrangement, it becomes possible to easily inflate the elastic bag 20 while keeping a flat shape as a whole. In this case, a reinforcement effect of the elastic bag 20 can also be obtained by the highly stiff panel.

Hereinafter, a second embodiment of the liquid medicine continuous infuser according to the present invention will be explained next with reference to FIGS. 7A to 8.

Figure 7A:
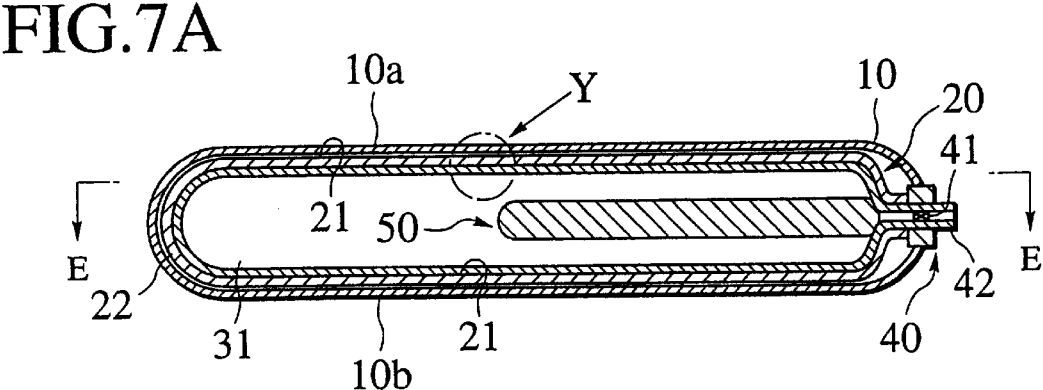
FIG. 7A is a side cross-sectional view for showing a state of a liquid medicine continuous infuser charged with a liquid medicine according to a second embodiment of the present invention.
Figure 7B:
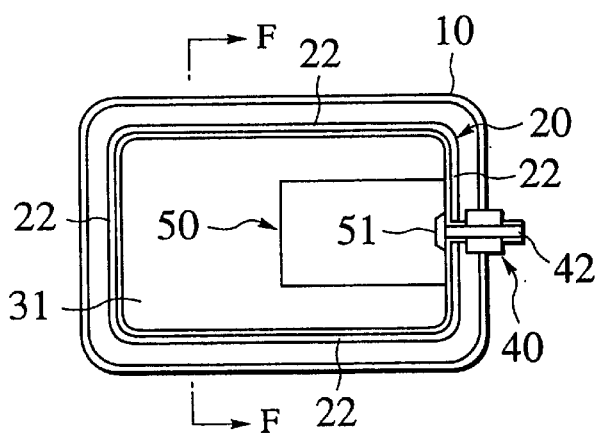
FIG. 7B is a cross-sectional view cut along an E—E line of FIG. 7A.
Figure 7C:
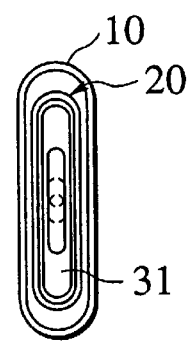
FIG. 7C is a cross-sectional view cut along an F—F line of FIG. 7B.
Figure 7D:
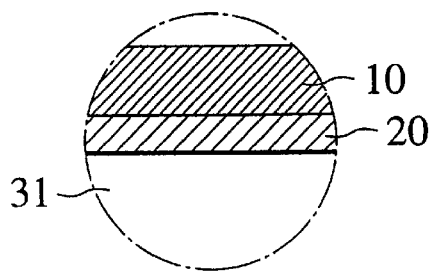
FIG. 7D is an enlarged cross-sectional view of a Y portion of FIG. 7A.
Figure 8:
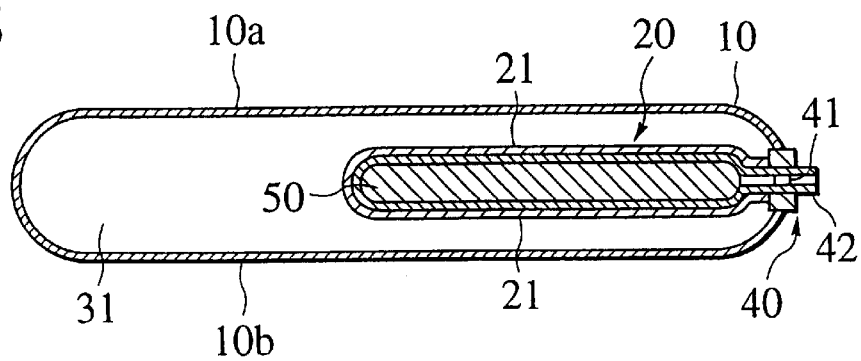
FIG. 8 is a side cross-sectional view for showing a state of the liquid medicine continuous infuser with the liquid medicine flowed out completely in the same embodiment.

FIGS. 7A to 7D show a state of the liquid medicine continuous infuser filled with a liquid medicine; FIG. 7A is a side cross-sectional view, FIG. 7B is a cross-sectional view cut along an E—E line of FIG. 7A, FIG. 7C is a cross-sectional view cut along an F—F line of FIG. 7B, FIG. 7D is an enlarged cross-sectional view of a Y portion of FIG. 7A, and FIG. 8 is a side cross-sectional view for showing a state of the liquid medicine continuous infuser with the liquid medicine flowed out completely. Those portions practically identical with portions of the first embodiment are attached with the same reference symbols by omitting a detailed explanation thereof.

According to the present embodiment, there is not provided the inner bag as described in the first embodiment and a liquid medicine is filled directly into an elastic bag 20. A cylindrical liquid medicine inflow/outflow opening 40 is integrally formed with one end of a peripheral wall 22 in the longitudinal direction of the elastic bag 20. This liquid medicine inflow/outflow opening 40 is stretched to the outside from one end of a protection case 10 in its longitudinal direction. A check valve 41 is provided within the liquid medicine inflow/outflow opening 40.

The present embodiment is characterized in that there is inserted into the elastic bag 20 a core 50 having a larger volume than a content capacity of the elastic bag 20 in its free state. As such a core 50, it is possible to use a solid unit body made of a synthetic resin or a metal, or a bag member filled with a gas, a liquid or the like. In the case of a solid core, the inside of this core can be hollowed to reduce the weight. It is preferable that the core 50 has a shape easily adaptable to an inner peripheral shape of the elastic bag 20 when the elastic bag 20 is shriveled. Further, there may be provided a recess 51 or the like at an end of the core 50 in order to prevent the liquid medicine inflow/outflow opening 40 from being closed by the core 50.

In the present embodiment, the content capacity of the elastic bag 20 is set to the state of r2 in FIG. 1 by the volume of the core 50 even in the state that a liquid medicine 31 is not filled in the elastic bag 20. When the liquid medicine 31 is filled into the elastic bag 20, the content capacity of the elastic bag 20 becomes the state of r3 in FIG. 1. Once the medication of the liquid medicine 31 is started, the content capacity of the elastic bag 20 changes from the state of r3 to r2 as shown in the section of T4 in FIG. 1 along with the outflow of the liquid medicine 31.

As there is almost no change in the contraction pressure of the elastic bag 20 during the section shown by T4, it is possible to apply almost a constant pressing pressure to the inside liquid medicine 31 from the beginning to the end of the medication. As a result, it is possible to make the liquid medicine 31 outflow at almost a constant flow rate from the beginning to the end of the medication. Even if there is left almost no liquid medicine 31 within the elastic bag 20, the remaining liquid medicine 31 can be made to outflow to the last dip with almost no volume left in the elastic bag 20, as the pressing pressure is kept being applied to the liquid medicine 31.

In the present embodiment, the elastic bag 20 may also be structured by use of double bags, formed of an inner bag to be filled with the liquid medicine 31 and an external bag of an elastic material for applying a pressing pressure to the liquid medicine 31. In this case, the inner bag and the external bag may be integrally laminated to form a bag of a double-layer structure.

Further, it is also possible to employ in the present embodiment the elastic bag shown in FIGS. 5A and 5B or FIGS. 6A and 6B as explained in the first embodiment. Furthermore, it is also possible to employ the elastic bag provided with a highly stiff panel on the flat surface of the elastic bag.

Although preferred embodiments have been disclosed, modification would come within the scope of this invention. Thus, the claims should be studied to determine the true scope of this invention.

What is claimed is:

1. A liquid medicine continuous infuser, comprising:
    a bag-shaped member capable of applying a pressure to a liquid medicine accommodated inside said bag-shaped member, said pressure providing a predetermined characteristic curve in relation to a capacity of said bag-shaped member;
    an inflow/outflow section for flowing said liquid medicine in and out; and
    an area positioned inside said bag-shaped member and having a predetermined volume, said area making said bag-shaped member increase said capacity of said bag-shaped member when said liquid medicine is accommodated in said inside of said bag-shaped member, said bag-shaped member applying said pressure to said liquid medicine accommodated in said inside of said bag-shaped member along said predetermined characteristic curve, with a pressure used as an initial value and corresponding to said capacity increased by said area when said liquid medicine is accommodated in said inside of said bag-shaped member.

2. A liquid medicine continuous infuser according to claim 1, further comprising an inner bag to be filled with said liquid medicine in an inside thereof, wherein said bag-shaped member is an elastic bag and said area is formed by a fluid disposed between said elastic bag and said inner bag.

3. A liquid medicine continuous infuser according to claim 2, wherein a sum of a volume of said fluid and a volume of said inner bag when said inner bag is shriveled completely is larger than a capacity of said elastic bag in a relaxed state thereof.

4. A liquid medicine continuous infuser according to claim 1, wherein said bag-shaped member is an elastic bag and said area is formed by a core disposed inside said elastic bag.

5. A liquid medicine continuous infuser according to claim 4, wherein a volume of said core is larger than a capacity of said elastic bag in its relaxed state.

6. A liquid medicine continuous infuser according to claim 1, wherein said bag-shaped member is an elastic bag and said elastic bag has a pair of mutually opposite flat surfaces and a peripheral wall for connecting said pair of flat surfaces thereby forming a flat bag shape as a whole, and a thickness of each of said pair of flat surfaces is larger than a thickness of said peripheral wall at least at a center portion of each of said pair of flat surfaces.

7. A liquid medicine continuous infuser according to claim 6, wherein said thickness of each of said pair of flat surfaces gradually decreases in the vicinity of a portion where said pair of flat surfaces are connected to said peripheral wall.

8. A liquid medicine continuous infuser according to claim 1, wherein said bag-shaped member is an elastic bag and said elastic bag has a pair of mutually opposite flat surfaces and a peripheral wall for connecting said pair of flat surfaces thereby forming a flat bag shape as a whole, and there is provided a panel-shaped member having a higher stiffness than that of said elastic bag on said pair of flat surfaces.

9. A liquid medicine continuous infuser according to claim 1, wherein said inflow/outflow section is an inflow/outflow section provided corresponding to said peripheral wall of said elastic bag.

* * * * *